June 11, 1946. J. D. BROWNELL Plant Pat. 696
ROSE PLANT
Filed Feb. 19, 1945
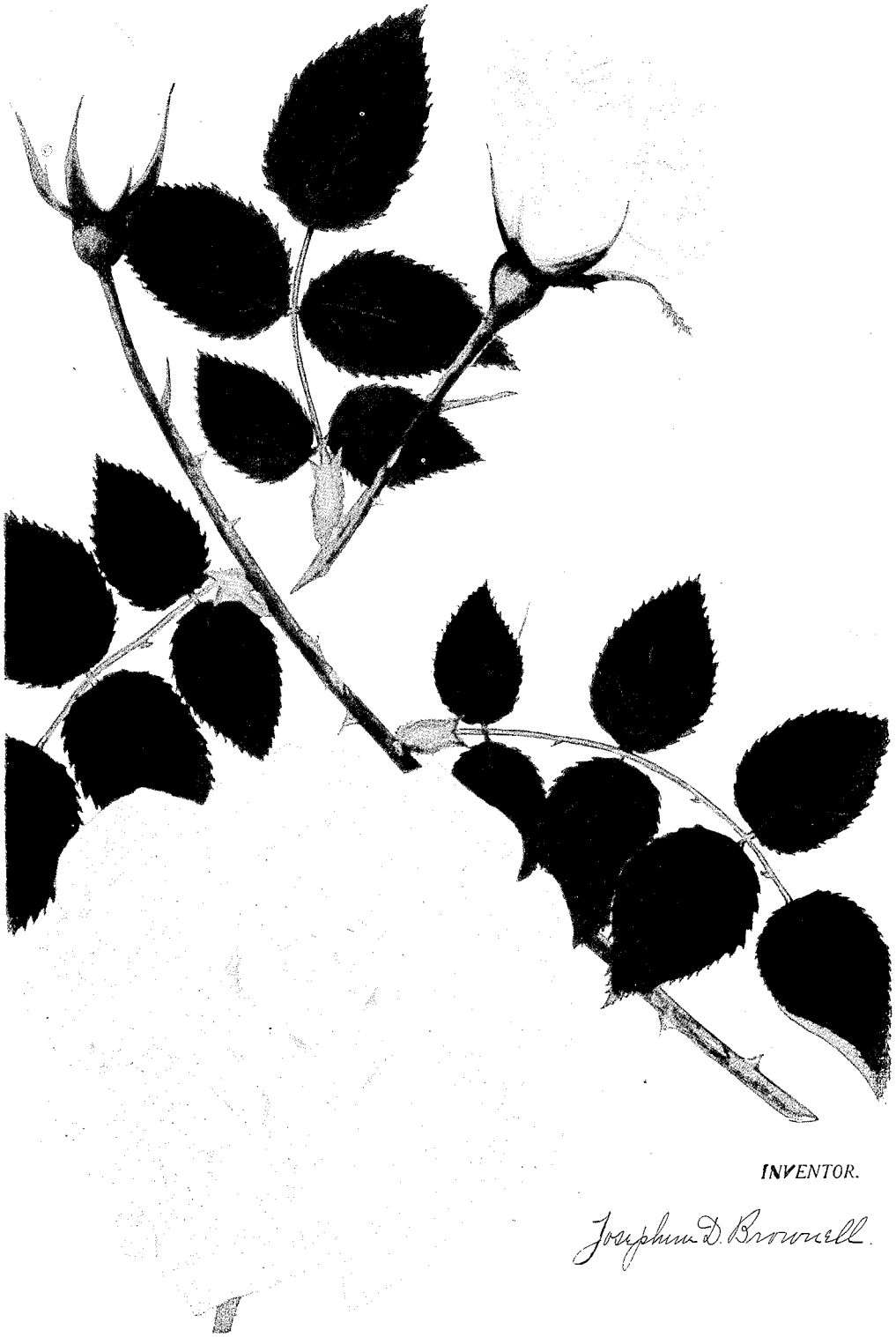
INVENTOR.
Josephine D. Brownell Patented June 11, 1946 Plant Pat. 696

UNITED STATES PATENT OFFICE

696

ROSE PLANT

Josephine D. Brownell, Little Compton, R. I.

Application February 19, 1945, Serial No. 579,589

1 Claim. (Cl. 47—61)

My invention relates to roses and especially to a new, original and distinct variety of the class known commercially as hardy climbing roses and to a type thereof known as large flowering *Rosa wichuraiana* hybrid; and also a further type known as hardy everblooming climbing roses; invented and discovered by me and under my direction in growing fields where plants were being grown for distribution and to the objective variety herein described, which can be and has been asexually reproduced.

My new rose is new as to the following characteristics; as to their joint association in connection with the characteristics of hardiness and immunity from serious injury on account of cold temperatures prevailing in certain parts of the northern portion of the United States:

The unique orange toned color of the petals, being approximately spectrum orange (ordinary dictionary definition) in total effect of both sides of the petals;

The multiple petals and variation within certain definite limits of the form of the bloom;

Its character of fragrance;

Its climbing and branching habit;

And especially its habit of blooming continuously or intermittently from early bloom time until frost.

This new rose variety is a variation or sport which occurred on a plant of the variety in commerce known as the variety "Break O'Day," being a dwarf hybrid tea. The variation consisted in a change from hybrid tea character to an everblooming climber character. There was no change in the form or other character of the flower, the only change being a change in the blooming character from the everblooming dwarf character of the hybrid tea to the reblooming or everblooming character common to the climbing hybrid tea class of roses.

I otherwise describe my new rose as follows:

It is a large flowered hardy climbing hybrid *Rosa wichuraiana*, crossed in its ancestral generations with, in addition to *Rosa wichuraiana*, several hybrid tea and species roses.

It is otherwise described as follows:

*Essential information*

Type: Hardy climbing; outdoor; sport; for cut flowers, garden display and for pot forcing.

Class: Hybrid climbing wichuraiana; type, large flowered climber.

Breeding or discovery: The discovery of this new rose was made by me and by my assistants and co-workers on the first day of November, 1940,[1] in the field where the hybrid tea variety "Break O'Day" was being grown; the stem which first expressed this variation was cut and removed from the plant on which it grew and the eyes on the stem thereof were promptly budded on *Rosa multiflora* root stock; and also in the same propagating fields. The following spring these eyes developed and grew, and contrary to the procedure in such cases with once bloom climber eyes, they later set bloom stems which matured and bloomed flowers at the normal bloom time and frequently thereafter throughout the growing season and during this same period also grew climber canes common to once bloom climbers. These plants continued throughout the season at various times to rebloom and produce flowers in the manner common to the dwarf hybrid tea. Eyes from second clonal generation similarly budded produced flowers throughout the growing season. Thus these propagations have reproduced the character of rebloom originally discovered in the sport or variation described.

The hybrid tea variety Break O'Day, from which my new rose sported, may be described as to its characteristics in common with my new rose, as follows:

It was produced by me and under my direction by breeding.

It has inherited from *Rosa wichuraiana* hardiness or immunity from serious injury on account of cold temperatures prevailing in certain parts of the northern United States.

Its *petals* are of the color orange (ordinary dictionary definition) with an unusual brilliance and luster, with a tendency to hold this color under exposure.

The *form* of the bloom is new and varies within certain definite limits, it opens ovoid, high centered and recurled, it holds that form for a long time and the flowers open large, often to five inches and some are larger.

It has a distinct *fragrance*, being a combination of China tea and wichuraiana.

It is remontant and everblooming or reblooming.

It is free flowering.

It ascends in height by recurrent branching.

In the accompanying drawing it is shown in its natural colors, that is, as near as is possible to do so artificially.

In the drawing forming a part of this specification is shown a leaf with seven leaflets being characteristic of Break O'Day.

Foliage: Is abundant to normal of compound leaves usually of three or five leaflets near the flower, five leaflets farther down the stem and frequently seven leaflets near the base. Size of leaflets medium hybrid tea size. Form of leaflets usually ovate with apex moderately acute, slightly variable, base rounded on short petiolules; margins slightly irregularly serrated

[1] This and other dates herein are approximate.

of meduim sized and pointed serrations. Color of leaflets on the upper surface is usually from Dusky Yellowish Green[1] to Dark Dull Yellow Green and the reverse side is substantially Asphodel Green. The young growths more nearly compare both sides with the color of the under sides of the leaflets with edges of traces of overlay of Indian Red to Dahlia Carmine and lighter, the latter soon disappearing as growth develops.

The *rachises* are medium, moderately narrow to slender, upper side smooth except some very short reddish hairs, grooved, under side, moderately smooth with some hairs and usually three to five short prickles of a light greenish shade (ordinary dictionary definition).

*Stipules* are medium averaging about three quarters of an inch long, usually wider at the center, with medium points, the upper edges of which when spaced in the same plane make an angle varying from 90 to 110 degrees.

*Disease*; usually resistant to mildew and considerably resistant to blackspot.

Growth: Habit, dwarf becoming bushy. The growth is moderately free at first, developing after one or two years under favorable vegetative opportunity, extreme vigor. The canes and branches are medium in the young plants deevloping in older plants from medium to very vigorous.

*Mature stems,* color same as upper surface of leaves, shading variously lighter and to more reddish and to color of under sides of leaves. *Prickles,* several, usually three to five between leaves, length averaging about 3/8 of an inch, bronze to red, shading from Dahlia Carmine to lighter at the base, turning lighter throughout and later nearly colorless, tips nearly straight. Hairs on upper portions of stems usually same color as prickles. Tip of very young branches color of prickles rapidly changing to color of main stem.

Bud: Neck normal to more rigid and slightly thicker; opens well, being little to not at all affected by hot or wet weather or both, as to color and form, except at very high temperatures the color is less intense and the form of the petals on opening is less recurled.

Before the calyx breaks the *size* is medium, *form* ovoid, tip pointed, frequently with one or more sepals with foliaceous parts extending beyond the apex up to about one half inch, the number and size of the foliaceous appendages being variable and frequently having one narrow pointed appendage on each side of the sepals, otherwise the sepals are usually normal and regular, tapering to nearly lanceolate near the apex, which turn back nearly perpendicular to the pedicel as the bud opens.

*Color* of the bud as the calyx opens, outside of petals, top border center is Pale Yellow Orange, this border color varies in width from about 1/16 to 1/32 of an inch and extends about half way down the petals on both sides. Below and inside this border the color is Pale Yellow Orange to Orange Buff overlaid with Grenadine Pink. The extreme base is Buff Yellow. The color intensity of the bud and of the flower is slightly variable under different environments, and the color descriptions herein are a substantial average of that variability under favorable conditions, collectively averaging orange in color (ordinary dictionary definition).

[1] Color references herein unless otherwise specified are to Ridgway.

Bloom: Has petals variable in number, usually from 40 to 60 with some narrow petals and petaloids in the center variable in number. The flower opens without showing the stamens and pistils until late maturity, the diameter of the flower when fully open is approximately 5 inches. The petals are variable from obovate to ovate with inner petals narrow irregular variable forms, outer and intermediate petals, except in extremely hot temperatures, recurl outward, frequently notched once at the apex. Texture is medium to thick and leathery, both sides slightly satiny to shiny.

The *outer petals* and the exposed borders show less color intensity than the rest of the open flower and the color intensity increases progressively toward the center and is slowly lessened each day from exposure as the flower opens. The time of opening in favorable conditions is frequently five days.

The *petals* are substantial and after about five to six days drop off cleanly, except that occasionally one or two inner petals or petaloids cling to turn colorless to drop later. The flower does not usually ball in wet weather.

Reproductive organs:

*Stamens,* quantity variable, indirectly proportionate to the number of petals, usually few, of uneven medium length.

*Anthers,* Light Salmon Orange.

*Filaments,* nearly Mustard Yellow.

*Pistils* are several, of slight uneven length about 1/2 inch long.

*Styles* are Chalcedony Yellow.

*Stigmas* are Citron Yellow, the pollen is moderate in quantity.

*Ovaries* are usually all enclosed, occasionally one or more protrude.

*Hips* frequently develop, ovoid to globular with inconspicuous neck. Color nearly like under side of leaves with variable overlay on the sunny side, moderately smooth, walls thin, fleshy.

*Sepals* are persistent and break off easily.

*Seeds* variable in number, germination nearly nil.

Breeding: The seed parent of Break O'Day is "Glendale" and its pollen parent is a variety long grown by me and is believed to be a sport of "Miss Lolita Armour."

The date of the pollen cross that produced Break O'Day was approximately July 1, 1931, the seed was planted December 20, 1931, and the date of the first flower was August 5, 1932. Extensive propagations thereof have been made.

Plants of this variety budded from the seedling on *Rosa Multiflora* root stock, have after tops having been entirely exposed above ground from the budded eye up, to moderate sub-zero temperatures from zero to twelve below Fahrenheit, survived and bloomed normally the following season in the hybrid tea manner.

Propagation: My new rose has held its distinguishing characteristics through succeeding propagations by budding.

Genetic viewpoint: From a genetic viewpoint it is to be noted that this variation or bud sport is a change in the expression of the factors for vegetative and for sexual expression. This type of expression is not common to the hybrid tea or to tall growing *Rosa wichuraiana* climber forms or to any recombination thereof through inheritance; but is frequently effected through the processes of Nature (commonly called a bud sport) by propagating through several propagating generations with the selection of propagating eyes only from the base of the bloom stems of a hybrid tea variety.

Plant height: Plants of my new rose frequently attain a height of 15 feet or more after a few years of favorable growth.

*Flower*

Habit: My new rose blooms out of doors in Little Compton, Rhode Island, in late June and July and begins to bloom about five days before the variety "Mary Wallace" begins to bloom.

Flowers borne: The flowers that are borne singly to five, occasionally more, in regular hybrid tea type of clusters, usually develop consecutively a few days' maturity apart, on strong stiff woody stems, varying in length up to 15 to 20 or more inches.

Quantity of bloom: Abundant out of doors in full sunshine, not materially reduced by covering established plants with clean earth for winter protection. It blooms the year after transplanting when promptly planted.

Continuity: Intermittently from bloom time until heavy frost.

Comparisons: The hardy climbing everblooming rose variety in commerce most closely resembling this new rose variety is "New Dawn" Plant Patent No. 1. My new rose is distinctly different from New Dawn in that New Dawn is of a shell pink, its petals are usually less recurled, and the new rose has fragrance of a more China tea nature. The bloom and rebloom habits are substantially the same as those of climbing sport varieties from hybrid teas other than *Rosa wichuraiana* hybrids, a class known commercially as Climbing Hybrid Teas.

I claim:

The variety of hardy *Rosa wichuraiana* hybrid plant substantially as herein disclosed, characterized by the features of its parent variety Break O'Day with the additional features of climbing habit and intermittent rebloom until frost.

JOSEPHINE D. BROWNELL.